(12) United States Patent
Sun et al.

(10) Patent No.: US 10,588,888 B2
(45) Date of Patent: Mar. 17, 2020

(54) CNS-ACCESSIBLE PHARMACOLOGICAL CHAPERONES FOR TREATMENT OF ACID β-GLUCOSIDASE-RELATED DISEASE STATES

(71) Applicant: Children's Hospital Medical Center, Cincinnati, OH (US)

(72) Inventors: Ying Sun, Mason, OH (US); Zhaolin Wang, Wellesley, MA (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 16/036,020

(22) Filed: Jul. 16, 2018

(65) Prior Publication Data
US 2019/0015380 A1  Jan. 17, 2019

Related U.S. Application Data

(60) Provisional application No. 62/533,212, filed on Jul. 17, 2017.

(51) Int. Cl.
| | |
|---|---|
| *A61K 31/341* | (2006.01) |
| *A61K 31/443* | (2006.01) |
| *A61K 31/501* | (2006.01) |
| *A61K 31/4155* | (2006.01) |
| *A61K 31/351* | (2006.01) |
| *A61P 25/16* | (2006.01) |
| *A61P 43/00* | (2006.01) |
| *A61K 9/00* | (2006.01) |
| *A61K 31/49* | (2006.01) |
| *A61K 31/445* | (2006.01) |
| *A61K 31/4025* | (2006.01) |

(52) U.S. Cl.
CPC .......... *A61K 31/341* (2013.01); *A61K 9/0053* (2013.01); *A61K 31/351* (2013.01); *A61K 31/4155* (2013.01); *A61K 31/443* (2013.01); *A61K 31/501* (2013.01); *A61P 25/16* (2018.01); *A61P 43/00* (2018.01); *A61K 31/4025* (2013.01); *A61K 31/445* (2013.01); *A61K 31/49* (2013.01); *A61K 2300/00* (2013.01)

(58) Field of Classification Search
CPC .................................................. A61K 31/341
See application file for complete search history.

(56) References Cited

PUBLICATIONS

Patnaik et al., Discovery, structure-activity relationship, and biological evaluation of noninhibitory small molecule chaperones of glucocerebrosidase, J Med Chem. Jun. 28, 2012;55(12):5734-48.*

Aflaki, E., et al., "A New Glucocerebrosidase Chaperone Reduces α-Synuclein and Glycolipid Levels in iPSC-Derived Dopaminergic Neurons from Patients with Gaucher Disease and Parkinsonism," J Neurosci, 2016, 36(28):7441-7452, 12 pgs.
Aymami, J., et al., "Pharmacological chaperones for enzyme enhancement therapy in genetic diseases," Pharm Pat Anal, 2013, 2(1):109-124, 16 pgs.
Bendikov-Bar, I., et al., "Ambroxol as a pharmacological chaperone for mutant glucocerebrosidase," Blood Cells Mol Dis, 2013, 50(2):141-145, 5 pgs.
Depaolo, J., et al., "The Association Between Mutations in the Lysosomal Protein Glucocerebrosidase and Parkinsonism," Movement Disorders: Official Journal of the Movement Disorder Society, 2009, 24(11):1571-1578, 8 pgs.
Khanna, R., et al., "The pharmacological chaperone isofagomine increased the activity of the Gaucher disease L444P mutant form of β-glucosidase," FEBS J, 2010, 277(7):1618-1638, 21 pgs.
Marugan, J.J., et al., "Non-iminosugar glucocerebrosidase small molecule chaperones," MedChemComm, 2012, 3(1):56-60, 5 pgs.
Mazzulli, J.R., et al., "Gaucher's Disease Glucocerebrosidase and α-synuclein form a bidirectional pathogenic loop in synucleinopathies," Cell, Jul. 2011, 146(1):37-52, 28 pgs.
Patnaik, S., et al., "Discovery, Strucure-Activity Relationship, and Biological Evaluation of Noninhibitory Small Molecule Chaperones of Glucocerebrosidase," J Med Chem, 2012, 55(12):5734-5748, 15 pgs.
Richter, F., et al., "A GCase Chaperone Improves Motor Function in a Mouse Model of Synucleinopathy," Neurotherapeutics, 2014, 11(4):840-856, 17 pgs.
Sidransky, E., et al., "Multicenter Analysis of Glucocerebrosidase Mutations in Parkinson's Disease," The New England Journal of Medicine, 2009, 361(17):1651-1661, 11 pgs.
Sun, Y., et al., "Ex Vivo and In Vivo Effects of Isofagomine on Acid β-Glucosidase Variants and Substrate Levels in Gaucher Disease," J Biol Chem, 2012, 287(6):4275-4287, 13 pgs.
Sun, Y., et al., "Isofagomine In Vivo Effects in a Neuronopathic Gaucher Disease Mouse," PloS one, 2011, 6(4):e19037, 12 pgs.
Sun, Y., et al., "Neuronopathic Gaucher disase in the mouse: viable combined selective saposin C deficiency and mutant glucocerebrosidase(V394L) mice with glucosylsphingosine and glucosylceramide accumulation and progressive neurological deficits," Human Molecular Genetics, 2010, 19(6):1088-1097, 10 pgs.
U.S. Appl. No. 62/533,212, filed Jul. 17, 2017.

* cited by examiner

*Primary Examiner* — Svetlana M Ivanova
(74) *Attorney, Agent, or Firm* — Frost Brown Todd LLC; Nicole M. Tepe

(57) ABSTRACT

Disclosed herein are β-glucosidase (GCase) chaperones and methods of using GCase chaperones in an individual in need thereof. GBA1 mutations lead to GCase deficiency and substrate accumulation, causing Gaucher disease. Currently, no FDA or EMA-approved therapeutic for neuronopathic Gaucher disease is available. Improved GCase activity in brain cells using a chaperone may reduce substrate accumulation and associated pathology. Disclosed herein are novel non-inhibitory chaperone compounds of GCase that have properties of a central nervous system drug. Those compounds effectively restored mutant GCase activity by stabilizing protein and enhancing lysosomal localization and may be useful for chaperone therapy to treat neuronopathic Gaucher disease and likely to Parkinson's disease.

8 Claims, 8 Drawing Sheets

CNS-ACCESSIBLE PHARMACOLOGICAL CHAPERONES FOR TREATMENT OF ACID β-GLUCOSIDASE-RELATED DISEASE STATES

CROSS-REFERENCE TO RELATED APPLICATIONS

This application claims priority to and benefit of U.S. Provisional Application Ser. No. 62/533,212, filed Jul. 17, 2017 and entitled "CNS-accessible pharmacological chaperones for treatment of neuronopathic Gaucher disease and Parkinson's disease," the contents of which is incorporated in its' entirety for all purposes.

BACKGROUND

Neuronopathic Gaucher disease patients have shortened life expectancy. Accumulation of lipids substrates and inflammation causes neurodegeneration in neuronopathic Gaucher disease. Mutations in GBA1, the gene responsible for Gaucher disease, are the most common known genetic risk factors for Parkinson's disease. There are no FDA or EMA-approved therapeutic for neuronopathic Gaucher disease and Parkinson's disease currently available, representing unmet medical needs.

GCase is a druggable target for chaperon therapy. Small molecule pharmaceutical chaperone can be made into an oral drug which can penetrate to the brain and restore mutant GCase. Improved GCase activity by chaperone in brain cells will reduce substrate accumulation, inflammation, mitigate alpha-synuclein pathology and improve sensorimotor and cognitive function. The novel non-inhibitory pharmaceutical chaperons will meet pressing needs for neuronopathic Gaucher disease, it is expected that the benefit of this chaperone therapy will apply to Parkinson's disease.

Conventional enzyme replacement therapy with pharmacologic GCase has been a modestly successful treatment in visceral type Gaucher disease. Because GCase is a very unstable enzyme, patients have to be administered by intravenous infusion very frequently to maintain therapeutic efficacy. The chaperone stabilizes GCase allowing prolonged drug efficacy. This provides a commercial opportunity to improve current enzyme replacement therapy for visceral forms of Gaucher disease, for example, and reduce the burden on the patients.

BRIEF SUMMARY

Disclosed herein are β-glucosidase (GCase) chaperones and methods of using GCase chaperones in an individual in need thereof. GBA1 mutations lead to GCase deficiency and substrate accumulation, causing Gaucher disease. Currently, no FDA or EMA-approved therapeutic for neuronopathic Gaucher disease is available. Improved GCase activity in brain cells using a chaperone may reduce substrate accumulation and associated pathology. Disclosed herein are novel non-inhibitory chaperone compounds of GCase that have properties of a central nervous system drug. Those compounds effectively restored mutant GCase activity by stabilizing protein and enhancing lysosomal localization and may be useful for chaperone therapy to treat neuronopathic Gaucher disease and likely to Parkinson's disease.

BRIEF DESCRIPTION OF THE DRAWINGS

This application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

DETAILED DESCRIPTION

Definitions

Figure 1:
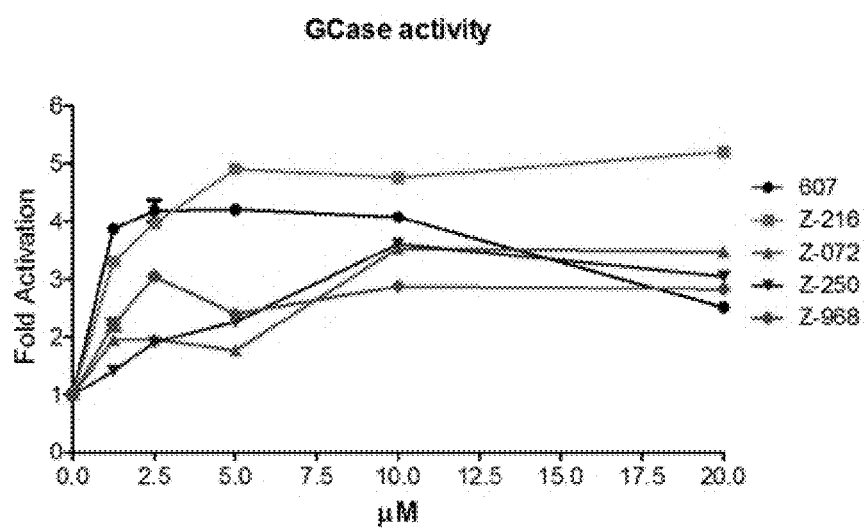
FIG. 1. Screen of small molecules with NCGC607 as a positive control. Mutant GCase (V394L) fibroblasts were incubated with small molecules for 5 days at various concentration. Compound 216 has superior activation function on GCase and reduced toxicity compared to 607.

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

The active agent may form salts, which are also within the scope of the preferred embodiments. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps, which may be employed during preparation. Salts of the compounds of the active agent may be formed, for example, by reacting a compound of the active agent with an amount of acid or base, such as an equivalent amount, in a medium such as one in which the salt precipitates or in an aqueous medium followed by lyophilization. When the compounds are in the forms of salts, they may comprise pharmaceutically acceptable salts. Such salts may include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

Disclosed herein are GCase chaperones and methods of using GCase chaperones in an individual in need thereof. GBA1 mutations lead to acid β-glucosidase (GCase) deficiency and substrate accumulation, causing Gaucher disease. Currently, no FDA or EMA-approved therapeutic for neuronopathic Gaucher disease is available. Improved GCase activity in brain cells using a chaperone may reduce substrate accumulation and associated pathology. Disclosed herein are novel non-inhibitory chaperone compounds of GCase that have properties of a central nervous system drug. Those compounds effectively restored mutant GCase activity by stabilizing protein and enhancing lysosomal localization and may be useful for chaperone therapy to treat neuronopathic Gaucher disease and likely to Parkinson's disease.

Gaucher disease is an inherited recessive genetic disorder and the most common lysosomal storage disease with a prevalence of 1/50,000 live births. In Gaucher disease, GBA1 mutations lead to defective GCase for sufficient lipid substrate degradation. Pharmacologic chaperones are small molecules that can promote normal or inhibit aberrant folding of mutant GCase [1]. Benefits of pharmacological chaperones may include oral convenience, nearly universal tissue penetration (particularly central nervous system, CNS), and avoidance of protein-associated immunologic side effects. Chaperone therapy can functionally recover mutant GCase by improving protein folding, stability and trafficking to lysosome, and to clear the accumulated disease substrate in patients who have amenable mutations, indicating it's potential as a therapeutic for Gaucher disease [2, 3]. GBA1 mutations are also the most common known genetic risk factor for Parkinson's disease [4, 5]. Applicant has found that there is a reciprocal interaction between GCase and alpha-synuclein levels [6], which supports a therapeutic option to increase GCase activity and therefore reduce alpha-synuclein levels and GCase misfolding to modify the course of Parkinson's disease. Thus, enhancing GCase in the brain is a therapeutic approach for Gaucher disease and Parkinson's disease.

Several small molecule chaperones have been reported previously. Isofagomine is a potent inhibitor of GCase and an effective chaperone of mutant GCases in fibroblasts and tissues of Gaucher and Parkinson disease models [3, 7]. However, Applicant and others have confirmed that, unfortunately, Isofagomine's ex vivo results of increasing GCase activity and protein are insufficient to improve in vivo substrate degradation due to its inhibition of GCase [2, 8]. Ambroxol, a commonly used expectorant which also has chaperone activity on GCase [9], is in Phase I trial only for the visceral form Gaucher disease (ClinicalTrials.gov-NCT01463215). Two non-inhibitory chaperones (NCGC607 and NCGC758) identified by NIH Scientists restore mutant GCase activity and protein [10-12]. NCGC607 also reduced alpha-synuclein levels in dopaminergic neurons suggesting its potential for neurological Gaucher and Parkinson's diseases. However, NCGC607 is a poor CNS entry compound and NCGC758 has weak chaperoning effect on GCase. Thus, those reported chaperones either act as an inhibitor of GCase or has limited CNS-accessibility that prohibit their medical use for neuronopathic Gaucher disease. Applicant screened the small molecules with NCGC607 as a control compound using mutant GCase fibroblasts and identified a compound (termed "216") having superior activation function on GCase. Applicant has found that the properties of the 216 compound are very close to the average properties of marketed CNS drugs. Applicant found that further optimization of the 216 compound lead to the discovery of its stereoisomers, "Compound 6" and "Compound 8." Compound 8 showed better activity than Compound 6 in the mutant GCase fibroblasts assay. Thus, it is believed that these compounds may have effective CNS penetration for chaperone therapy and demonstrate a significant improvement over the art.

In one aspect, a method of treating an individual having a disorder associated with defective GCase is disclosed. The method may comprise the step of administering a chaperone to an individual in need thereof, wherein the chaperone may have the structure:

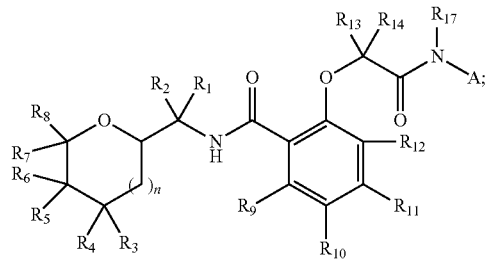

wherein

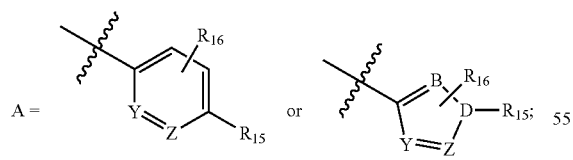

wherein R1, R2, R7, R8, R13, R14 are =O, or independently H, Cyano, or C1-4 Alkyl;

wherein R3, R4, R5, R6, R9, R10, R11, R12, R15, R16 are independently H, OH, NH2, NHR17, Cyano, C1-4 Alkyl or C1-4 Alkoxy;

wherein R17 is H, or Me;

wherein Y, Z, B, D are independently C or N; and wherein N=0 or 1.

In one aspect, the chaperone may have the structure:

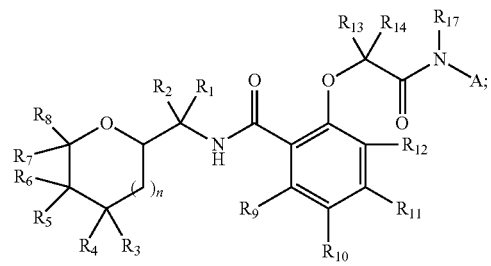

wherein A

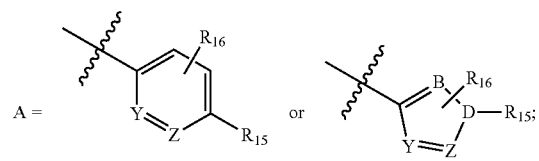

wherein R1, R2, R7, R8, R13, R14 are =O, or independently H, Cyano, or C1-4 Alkyl;

wherein R3, R4, R5, R6, R9, R10, R11, R12, R15, R16 are independently H, OH, NH2, NHR17, Halo, Cyano, C1-4 Alkyl or C1-4 Alkoxy;

wherein R17 is H, or Me;

wherein Y, Z, B, D are independently C or N;

wherein N=0 or 1.

In one aspect, the chaperone may have the structure:

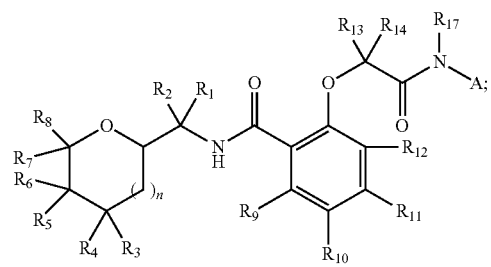

wherein A

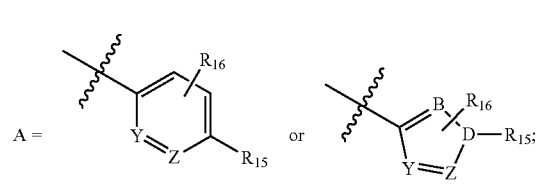

wherein R1, R2, R13, R14 are independently H, Me, or Et;

wherein R3, R4, R5, R6, R9, R10, R11, R12, R15, R16 are independently H, OH, NH2, NHR17, Halo, Cyano, Me, Et, OMe, or OEt;

wherein R17 is H, or Me;

wherein Y, Z, B, D are independently C or N; and wherein N=0 or 1.

In one aspect, the chaperone may have the structure:

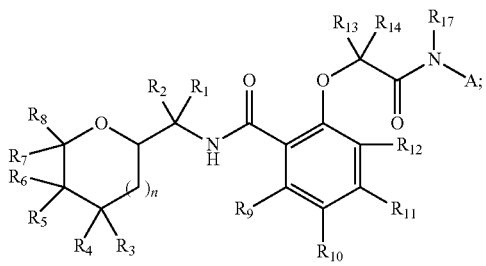

wherein A

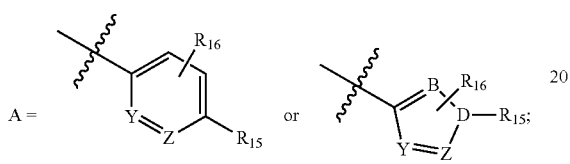

wherein R1, R2, R13, R14 are independently H, Me, or Et;
wherein R3, R4, R5, R6, R7, R8 are independently H, OH, or Me;
wherein R9, R10, R11, R12, R15, R16 are independently H, OH, NH2, NHR17, F, Cl, Br, Cyano, Me, Et, OMe, or OEt;
wherein R17 is H, or Me;
wherein Y=Z is C=N;
wherein B, D are N; and
wherein N=0 or 1.

In one aspect, the chaperone may have the structure:

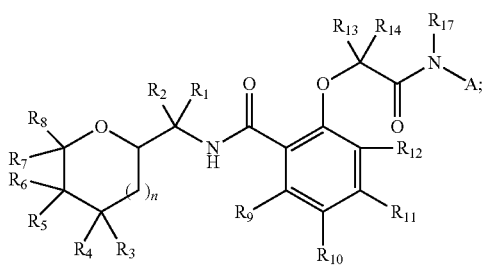

wherein

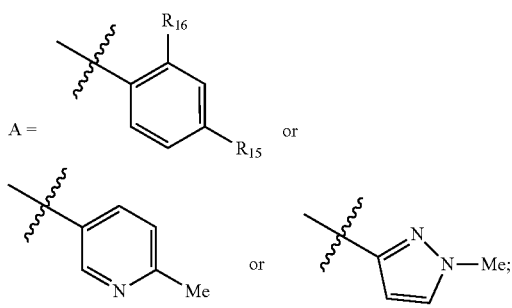

wherein R1, R2, R3, R4, R5, R6, R7, R8, R13, R14 are H;

wherein R9, R10, R11, R12 are independently H, OH, NH2, NHR17, F, Cl, Me, or OMe;
wherein R15, R16 are independently H, OH, F, Cl, Br, Me, or OMe;
wherein R17 is H, or Me; and
wherein N=0 or 1.

In one aspect, the chaperone may have the structure:

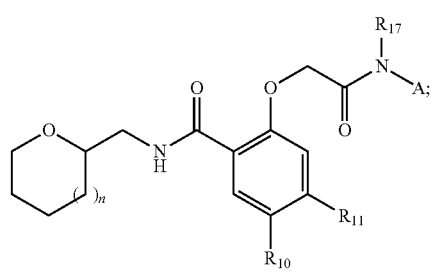

wherein A

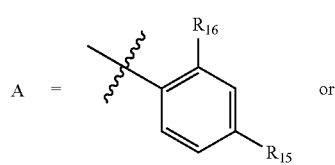

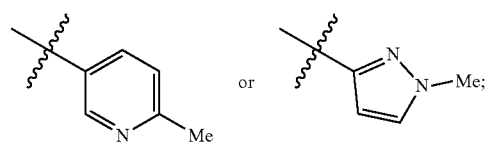

wherein R10, R11 are independently H, OH, NH2, NHR17, F, or Cl;
wherein R15 is H, F, Cl, or Br;
wherein R16 is F or OMe;
wherein R17 is H or Me; and
wherein N=0 or 1.

In one aspect, the chaperone may be selected from one or more of the following compounds:

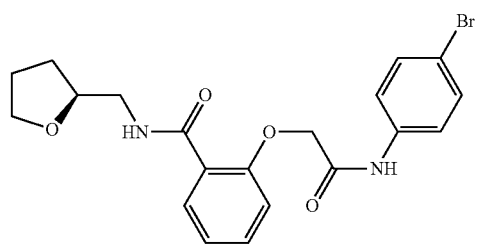 [SMILES: O=C(COc1ccccc1C(=O)NC[C@@H]1CCCO1)Nc1ccc(Br)cc1]

("Compound 8", 2-((4-bromophenylcarbamoyl)methyoxy)-N—(((S)-tetrahydrofuran-2-yl)methyl)benzamide);

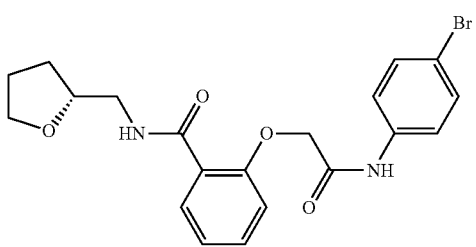 [SMILES: O=C(COc1ccccc1C(=O)NC[C@H]1CCCO1)Nc1ccc(Br)cc1]

("Compound 6", 2-((4-bromophenylcarbamoyl)methoxy)-N(((R)tetrahydrofuran-2-yl)methyl)benzamide));

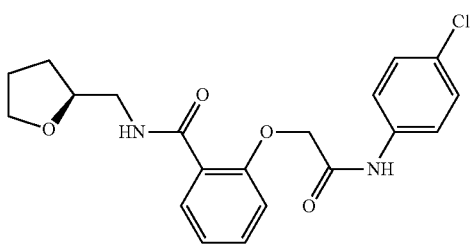 [SMILES: O=C(COc1ccccc1C(=O)NC[C@@H]1CCCO1)Nc1ccc(Cl)cc1]

("Compound 1", 2-((4-chlorophenylcarbamoyl)methoxy)-N—(((S)-tetrahydrofuran-2-yl)methyl)benzamide);

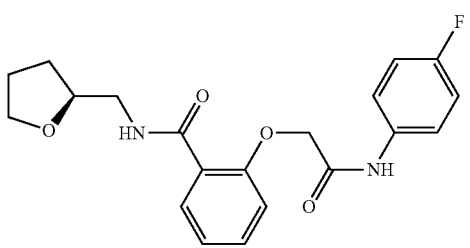

("Compound 2", 2-((4-fluorophenylcarbamoyl)methoxy)-N—(((S)-tetrahydrofuran-2-yl)methy)benzamide);

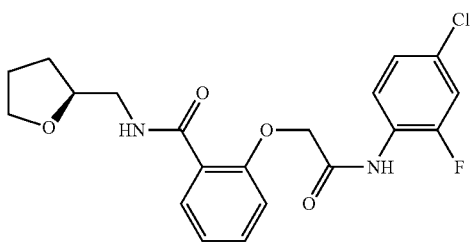 [SMILES: O=C(COc1ccccc1C(=O)NC[C@@H]1CCCO1)Nc1ccc(Cl)cc1F]

("Compound 3", 2-((4-chloro-2-fluorophenylcarbamoyl)methoxy)-N(((S)-tetrahydrofuran-2-yl)methyl)benzamide);

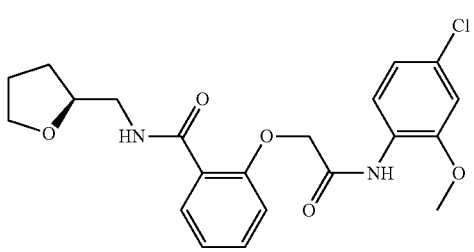 [SMILES: COc1cc(Cl)ccc1NC(=O)COc1ccccc1C(=O)NC[C@@H]1CCCO1]

("Compound 4", 2((4-chloro-2-methoxyphenylcarbamoyl)methoxy)-N—(((S)-tetrahydrofuran-2-yl)methyl)benzamide);

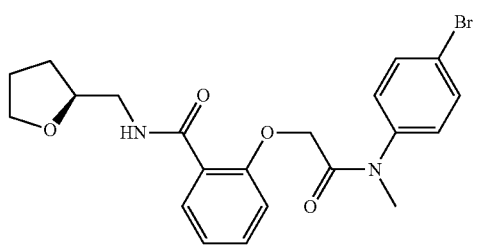 [SMILES: CN(C(=O)COc1ccccc1C(=O)NC[C@@H]1CCCO1)c1ccc(Br)cc1]

("Compound 5", 2-((N-4-bromophenyl)-N-methylcarbamoyl)methoxy)-N—(((S)-tetrahdrofuran-2-yl)methyl)benzamide);

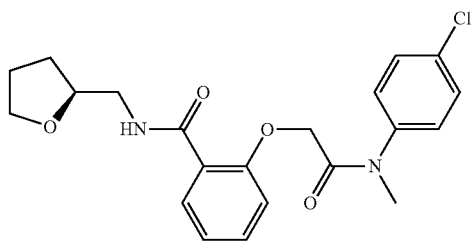 [SMILES: CN(C(=O)COc1ccccc1C(=O)NC[C@@H]1CCCO1)c1ccc(Cl)cc1]

("Compound 7", 2-((N-(4-chlorophenyl)-N-methylcarbamoyl)methoxy)N—(((S-tetrahdrofuran-2-yl)methyl)benzamide);

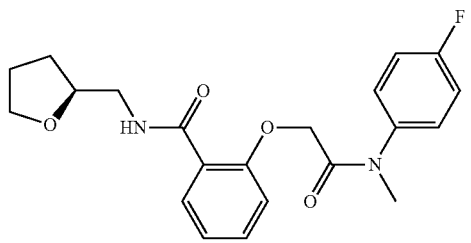 [SMILES: CN(C(=O)COc1ccccc1C(=O)NC[C@@H]1CCCO1)c1ccc(F)cc1]

("Compound 9", 2-((N-(4-fluorophenyl)-N-methylcarbamoyl)methoxy)-N—((S)-tetrahydrofuran-2yl)methyl)benzamide);

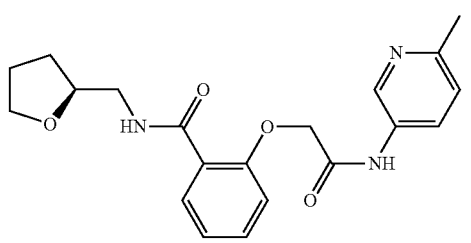 [SMILES: Cc1ccc(NC(=O)COc2ccccc2C(=O)NC[C@@H]2CCCO2)cn1]

("Compound 10", 2-((6-methylpyridin-3-ylcarbamoyl)methoxy)-N—(((S)-tetrahydrofuran-2-yl)methyl)benzamide);

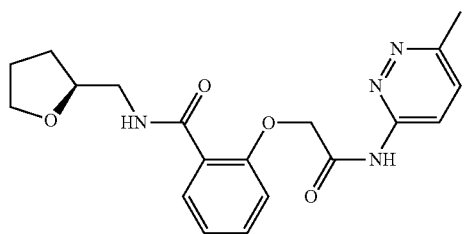 [SMILES: Cc1ccc(NC(=O)COc2ccccc2C(=O)NC[C@@H]2CCCO2)nn1]

("Compound 11", 2-((6-methylpyridazin-3-ylcarbamoyl)methoxy)-N—(((S)-tetrahydrofuran-2-yl))methyl)benzamide;

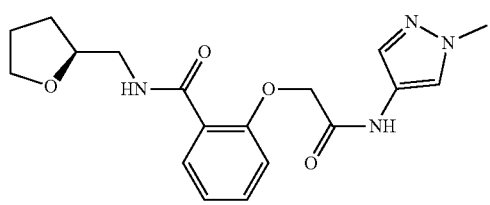 [SMILES: Cn1cc(NC(=O)COc2ccccc2C(=O)NC[C@@H]2CCCO2)cn1]

("Compound 12", 2-((1-methyl-1H-pyrazol-4-ylcarbamoyl)methoxy)-N—(((S)-tetrahdrofuran-2-yl)methyl)benzamide);

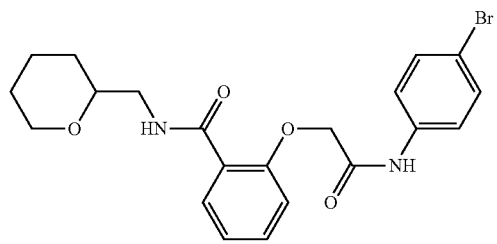 [SMILES: O=C(COc1ccccc1C(=O)NCC1CCCCO1)Nc1ccc(Br)cc1]

("Compound 13", 2-((4-bromophenylcarbamoyl)methoxy)-N-((tetrahydro-2H-pyran-2-yl)methyl)benzamide);

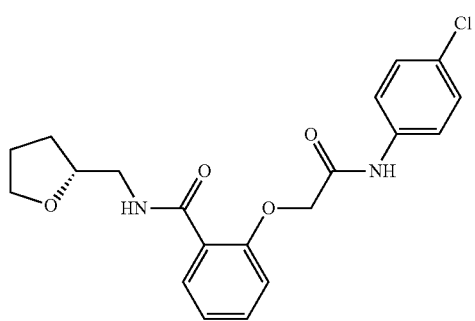 [SMILES: O=C(COc1ccccc1C(=O)NC[C@H]1CCCO1)Nc1ccc(Cl)cc1]

("Compound 14", 2-((4-chlorophenylcarbamoyl)methoxy)-N—(((R)-tetrahydrofuran-2-yl)methyl)benzamide);

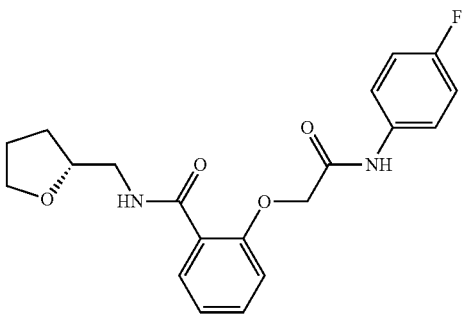 [SMILES: O=C(COc1ccccc1C(=O)NC[C@H]1CCCO1)Nc1ccc(F)cc1]

("Compound 15", 2-((4-fluorophenylcarbamoyl)methoxy)-N—(((R)-tetrahydrofuran-2-yl)methy)benzamide);

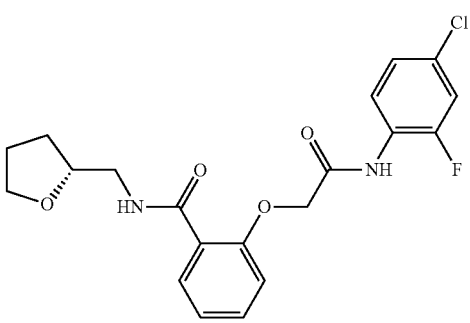 [SMILES: O=C(COc1ccccc1C(=O)NC[C@H]1CCCO1)Nc1ccc(Cl)cc1F]

("Compound 16", 2-((4-chloro-2-fluorophenyl carbamoyl)methoxy)-N(((R)-tetrahydrofuran-2-yl)methyl)benzamide);

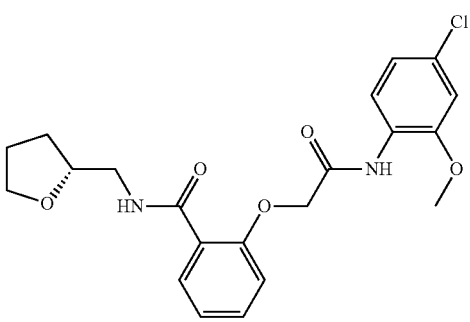 [SMILES: COc1cc(Cl)ccc1NC(=O)COc1ccccc1C(=O)NC[C@H]1CCCO1]

("Compound 17", 2((4-chloro-2-methoxyphenylcarbamoyl)methoxy)-N—(((R)-tetrahydrofuran-2-yl)methyl)benzamide);

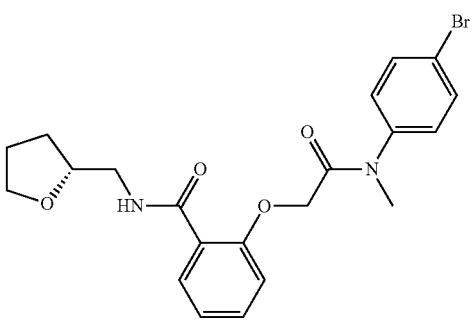 [SMILES: CN(C(=O)COc1ccccc1C(=O)NC[C@H]1CCCO1)c1ccc(Br)cc1]

("Compound 18", 2-((N-4-bromophenyl)-N-methylcarbamoyl)methoxy)-N—(((R)-tetrahdrofuran-2-yl)methyl)benzamide);

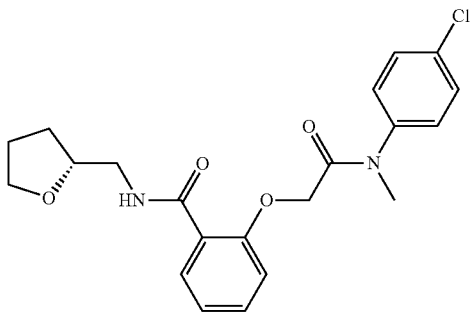 [SMILES: CN(C(=O)COc1ccccc1C(=O)NC[C@H]1CCCO1)c1ccc(Cl)cc1]

("Compound 19", 2-((N-(4-chlorophenyl)-N-methylcarbamoyl)methoxy N—(((R)-tetrahdrofuran-2-yl)methyl) benzamide);

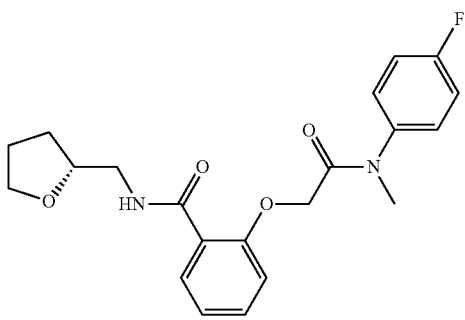 [SMILES: CN(C(=O)COc1ccccc1C(=O)NC[C@H]1CCCO1)c1ccc(F)cc1]

("Compound 20", 2-((N-(4-fluorophenyl)-N-methylcarbamoyl)methoxy)-N—(((R)-tetrahydrofuran-2yl)methyl)benzamide);

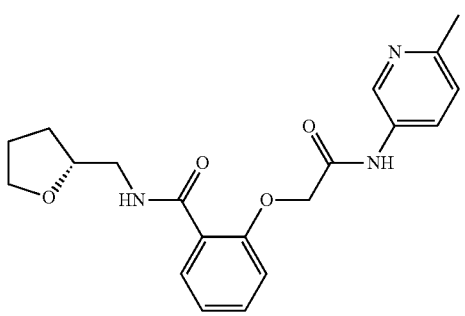

("Compound 21", 2-((6-methylpyridin-3-ylcarbamoyl) methoxy)-N—(((R)-tetrahydrofuran-2-yl)methyl)benzamide);

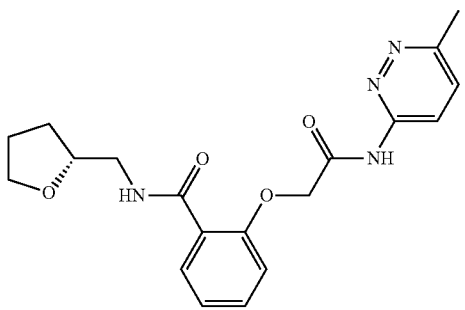 [SMILES: Cc1ccc(NC(=O)COc2ccccc2C(=O)NC[C@H]2CCCO2)cn1]

("Compound 22", 2-((6-methylpyridazin-3-ylcarbamoyl) methoxy)-N—(((R)-tetrahydrofuran-2-yl))methyl)benzamide;

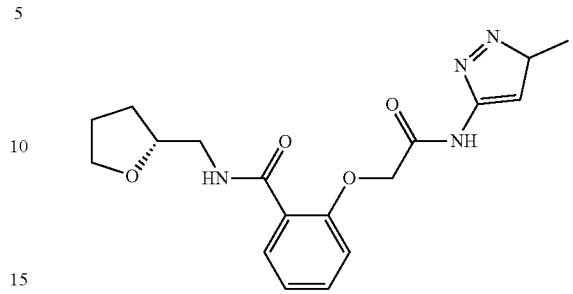

("Compound 23", 2-((1-methyl-1H-pyrazol-4-ylcarbamoyl) methoxy)-N—(((R)-tetrahdrofuran-2-yl)methyl)benzamide); or combinations thereof.

In one aspect, the chaperone may be the R enantiomer of any of the above-listed compounds.

In one aspect, the administration may be via oral administration.

In one aspect, the chaperone may be administered in an amount sufficient to functionally recover mutant GCase by one or more of improving protein folding, stability, and trafficking to lysosome.

In one aspect, the disorder may be selected from Parkinson's disease or Gaucher disease.

In one aspect, the chaperone may be used in combination with substrate reduction therapy (SRT), wherein the SRT may comprise administering a glucosylceramide synthase inhibitor in an amount sufficient for to degrade glucosylceramide. The combination of chaperone and SRT are believed to produce a synergistic effect, for example, in treating Gaucher disease. The chaperone enhances acid beta-glucosidase activity for degradation of substrate, glucosylceramide. The small molecule drug for SRT is an inhibitor of glucosylceramide synthase, and the combination of chaperone and SRT may provide a synergistic effect in treating disease such as Gaucher disease.

In one aspect, the administration may be for the treatment of Parkinson's disease in an individual in need thereof.

In one aspect, the administration may be for the treatment of Gaucher disease in an individual in need thereof.

In one aspect, a composition for the treatment of a disorder associated with defective GCase is disclosed. In this aspect, the composition may comprise a compound as described herein, a pharmaceutically acceptable excipient. The composition may further comprise a glucosylceramide synthase inhibitor. For example, the composition may include a glucosylceramide synthase inhibitor such as miglustat, eliglustat, Venglustat (Ibiglustar, Genzyme) and combinations thereof, as well as any glucosylceramide synthase inhibitor as would be known in the art.

In one aspect, active agents provided herein may be administered in a dosage form selected from intravenous or subcutaneous unit dosage form, oral, parenteral, intravenous, and subcutaneous. In some embodiments, active agents provided herein may be formulated into liquid preparations for, e.g., oral administration. Suitable forms include suspensions, syrups, elixirs, and the like. In some embodiments, unit dosage forms for oral administration include tablets and capsules. Unit dosage forms configured for administration once a day; however, in certain embodiments it may be desirable to configure the unit dosage form for administration twice a day, or more.

In one aspect, pharmaceutical compositions are isotonic with the blood or other body fluid of the recipient. The isotonicity of the compositions may be attained using sodium tartrate, propylene glycol or other inorganic or organic solutes. An example includes sodium chloride. Buffering agents may be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions may be maintained at the selected level using a pharmaceutically acceptable thickening agent. Methylcellulose is useful because it is readily and economically available and is easy to work with. Other suitable thickening agents include, for example, xanthan gum, carboxymethyl cellulose, hydroxypropyl cellulose, carbomer, and the like. In some embodiments, the concentration of the thickener will depend upon the thickening agent selected. An amount may be used that will achieve the selected viscosity. Viscous compositions are normally prepared from solutions by the addition of such thickening agents.

A pharmaceutically acceptable preservative may be employed to increase the shelf life of the pharmaceutical compositions. Benzyl alcohol may be suitable, although a variety of preservatives including, for example, parabens, thimerosal, chlorobutanol, or benzalkonium chloride may also be employed. A suitable concentration of the preservative is typically from about 0.02% to about 2% based on the total weight of the composition, although larger or smaller amounts may be desirable depending upon the agent selected. Reducing agents, as described above, may be advantageously used to maintain good shelf life of the formulation.

In one aspect, active agents provided herein may be in admixture with a suitable carrier, diluent, or excipient such as sterile water, physiological saline, glucose, or the like, and may contain auxiliary substances such as wetting or emulsifying agents, pH buffering agents, gelling or viscosity enhancing additives, preservatives, flavoring agents, colors, and the like, depending upon the route of administration and the preparation desired. Such preparations may include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components may influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions may be provided as a tablet, aqueous or oil suspension, dispersible powder or granule, emulsion, hard or soft capsule, syrup or elixir. Compositions intended for oral use may be prepared according to any method known in the art for the manufacture of pharmaceutical compositions and may include one or more of the following agents: sweeteners, flavoring agents, coloring agents and preservatives. Aqueous suspensions may contain the active ingredient in admixture with excipients suitable for the manufacture of aqueous suspensions.

Formulations for oral use may also be provided as hard gelatin capsules, wherein the active ingredient(s) are mixed with an inert solid diluent, such as calcium carbonate, calcium phosphate, or kaolin, or as soft gelatin capsules. In soft capsules, the active agents may be dissolved or suspended in suitable liquids, such as water or an oil medium, such as peanut oil, olive oil, fatty oils, liquid paraffin, or liquid polyethylene glycols. Stabilizers and microspheres formulated for oral administration may also be used. Capsules may include push-fit capsules made of gelatin, as well as soft, sealed capsules made of gelatin and a plasticizer, such as glycerol or sorbitol. The push-fit capsules may contain the active ingredient in admixture with fillers such as lactose, binders such as starches, and/or lubrimayts such as talc or magnesium stearate and, optionally, stabilizers.

Tablets may be uncoated or coated by known methods to delay disintegration and absorption in the gastrointestinal tract and thereby provide a sustained action over a longer period of time. For example, a time delay material such as glyceryl monostearate may be used. When administered in solid form, such as tablet form, the solid form typically comprises from about 0.001 wt. % or less to about 50 wt. % or more of active ingredient(s), for example, from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets may contain the active ingredients in admixture with non-toxic pharmaceutically acceptable excipients including inert materials. For example, a tablet may be prepared by compression or molding, optionally, with one or more additional ingredients. Compressed tablets may be prepared by compressing in a suitable machine the active ingredients in a free-flowing form such as powder or granules, optionally mixed with a binder, lubrimayt, inert diluent, surface active or dispersing agent. Molded tablets may be made by molding, in a suitable machine, a mixture of the powdered active agent moistened with an inert liquid diluent.

In some embodiments, each tablet or capsule contains from about 1 mg or less to about 1,000 mg or more of an active agent provided herein, for example, from about 10, 20, 30, 40, 50, 60, 70, 80, 90, or 100 mg to about 150, 200, 250, 300, 350, 400, 450, 500, 550, 600, 650, 700, 750, 800, or 900 mg. In some embodiments, tablets or capsules are provided in a range of dosages to permit divided dosages to be administered. A dosage appropriate to the patient and the number of doses to be administered daily may thus be conveniently selected. In certain embodiments two or more of the therapeutic agents may be incorporated to be administered into a single tablet or other dosage form (e.g., in a combination therapy); however, in other embodiments the therapeutic agents may be provided in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents may be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragamayth, or alginic acid or salts thereof.

Binders may be used to form a hard tablet. Binders include materials from natural products such as acacia, tragamayth, starch and gelatin, methyl cellulose, ethyl cellulose, carboxymethyl cellulose, polyvinyl pyrrolidone, hydroxypropylmethyl cellulose, and the like.

Lubrimayts, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, may be included in tablet formulations.

Surfactants may also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations may be employed wherein the active agent or analog(s) thereof is incorporated into an inert matrix that permits release by either diffusion or leaching mechanisms. Slowly degenerating matrices may also be incorporated into the formulation. Other delivery systems may include timed release, delayed release, or sustained release delivery systems.

Coatings may be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments may be added for identification or to characterize different combinations of active agent doses.

When administered orally in liquid form, a liquid carrier such as water, petroleum, oils of animal or plant origin such as peanut oil, mineral oil, soybean oil, or sesame oil, or synthetic oils may be added to the active ingredient(s). Physiological saline solution, dextrose, or other saccharide solution, or glycols such as ethylene glycol, propylene glycol, or polyethylene glycol are also suitable liquid carriers. The pharmaceutical compositions may also be in the form of oil-in-water emulsions. The oily phase may be a vegetable oil, such as olive or arachis oil, a mineral oil such as liquid paraffin, or a mixture thereof. Suitable emulsifying agents include naturally-occurring gums such as gum acacia and gum tragamayth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

Pulmonary delivery of the active agent may also be employed. The active agent may be delivered to the lungs while inhaling and traverses across the lung epithelial lining to the blood stream. A wide range of mechanical devices designed for pulmonary delivery of therapeutic products may be employed, including but not limited to nebulizers, metered dose inhalers, and powder inhalers, all of which are familiar to those skilled in the art. These devices employ formulations suitable for the dispensing of active agent. Typically, each formulation is specific to the type of device employed and may involve the use of an appropriate propellant material, in addition to diluents, adjuvants, and/or carriers useful in therapy.

The active ingredients may be prepared for pulmonary delivery in particulate form with an average particle size of from 0.1 μm or less to 10 μm or more, for example, from about 0.2, 0.3, 0.4, 0.5, 0.6, 0.7, 0.8, or 0.9 um to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 um. Pharmaceutically acceptable carriers for pulmonary delivery of active agent include carbohydrates such as trehalose, mannitol, xylitol, sucrose, lactose, and sorbitol. Other ingredients for use in formulations may include DPPC, DOPE, DSPC, and DOPC. Natural or synthetic surfactants may be used, including polyethylene glycol and dextrans, such as cyclodextran. Bile salts and other related enhancers, as well as cellulose and cellulose derivatives, and amino acids may also be used. Liposomes, microcapsules, microspheres, inclusion complexes, and other types of carriers may also be employed.

Pharmaceutical formulations suitable for use with a nebulizer, either jet or ultrasonic, typically comprise the active agent dissolved or suspended in water at a concentration of about 0.01 or less to 100 mg or more of active agent per mL of solution, for example, from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation may also include a buffer and a simple sugar (e.g., for protein stabilization and regulation of osmotic pressure). The nebulizer formulation may also contain a surfactant, to reduce or prevent surface induced aggregation of the active agent caused by atomization of the solution in forming the aerosol.

Formulations for use with a metered-dose inhaler device generally comprise a finely divided powder containing the active ingredients suspended in a propellant with the aid of a surfactant. The propellant may include conventional propellants, such as chlorofluorocarbons, hydrochlorofluorocarbons, hydrofluorocarbons, and hydrocarbons. Example propellants include trichlorofluoromethane, dichlorodifluoromethane, dichlorotetrafluoroethanol, 1,1,1, 2-tetrafluoroethane, and combinations thereof. Suitable surfactants include sorbitan trioleate, soya lecithin, and oleic acid.

Formulations for dispensing from a powder inhaler device typically comprise a finely divided dry powder containing active agent, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, for example, from about 5, 10, 15, 20, 25, 30, 35, 40, 45, or 50 wt. % to about 55, 60, 65, 70, 75, 80, 85, or 90 wt. % of the formulation.

In some embodiments, an active agent provided herein may be administered by intravenous, parenteral, or other injection, in the form of a pyrogen-free, parenterally acceptable aqueous solution or oleaginous suspension. Suspensions may be formulated according to methods well known in the art using suitable dispersing or wetting agents and suspending agents. The preparation of acceptable aqueous solutions with suitable pH, isotonicity, stability, and the like, is within the skill in the art. In some embodiments, a pharmaceutical composition for injection may include an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils may be employed conventionally as a solvent or suspending medium. For this purpose, any bland fixed oil may be employed including synthetic mono or diglycerides. In addition, fatty acids such as oleic acid may likewise be used in the formation of injectable preparations. The pharmaceutical compositions may also contain stabilizers, preservatives, buffers, antioxidants, or other additives known to those of skill in the art.

In some embodiments, the active agents provided herein may be provided to an administering physician or other health care professional in the form of a kit. The kit is a package which houses a container which contains the active agent(s) in a suitable pharmaceutical composition, and instructions for administering the pharmaceutical composition to a subject. The kit may optionally also contain one or more additional therapeutic agents currently employed for treating a disease state as described herein. For example, a kit containing one or more compositions comprising active agents provided herein in combination with one or more additional active agents may be provided, or separate pharmaceutical compositions containing an active agent as provided herein and additional therapeutic agents may be provided. The kit may also contain separate doses of an active agent provided herein for serial or sequential administration. The kit may optionally contain one or more diagnostic tools and instructions for use. The kit may contain suitable delivery devices, e.g., syringes, and the like, along with instructions for administering the active agent(s) and any other therapeutic agent. The kit may optionally contain instructions for storage, reconstitution (if applicable), and administration of any or all therapeutic agents included. The kits may include a plurality of containers reflecting the number of administrations to be given to a subject.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

General methods: All evaporations are carried out in vacuo with a rotary evaporator. Analytical samples are dried in vacuo (1-5 mmHg) at rt. Thin layer chromatography (TLC) is performed on silica gel plates, spots re visualized by UV light (214 and 254 nm). Purification by column and flash chromatography is carried out using silica gel (200-300 mesh). Solvent systems are reported as mixtures by volume. All NMR spectra are recorded on a Bruker 400 (400 MHz) spectrometer. $^1$H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on an Agilent 1200 series 6110 or 6120 mass spectrometer with electrospray ionization and excepted as otherwise indicated, the general LCMS condition was as follows: Waters X Bridge C18 column (50 mm*4.6 mm*3.5 um), Flow Rate: 2.0 mL/min, the column temperature: 40° C.

Specific condition for each compound:

Compound 2. 4-Bromoaniline (4.12 g, 23.95 mmol) is dissolved in 50 mL of dichloromethane in a round bottomed flask containing a stir bar. While stirring, triethylamine (2.91 g, 28.74 mmol) is added to the reaction mixture and then cooled to 0° C. 2-Chloroacetyl chloride (2.71 g, 23.95 mmol) is added dropwise to the reaction mixture, which is then allowed to slowly warm to room temperature and stirred for 16 hours. The reaction mixture is diluted with 100 mL of dichloromethane, washed twice with 1N HCl, run through a silica gel plug, and then concentrated in vacuo to give compound 2 as a white solid (2.25 g).

Compound 3. Potassium carbonate (3.75 g, 27.1 mmol) is added to a mixture of N-(4-bromophenyl)-2-chloroacetamide (2.25 g, 9.05 mmol) and methyl 2-hydroxybenzoate (1.38 g, 9.05 mmol) in DMF (30 mL). The reaction mixture is stirred for 16 hours. 1 N HCl is added slowly to the reaction mixture. The combined solution is extracted three times with ethyl acetate. The resulting organic layer is washed twice with water, once with brine, run through a silica plug, and then concentrated in vacuo to give a yellow solid. The solid is washed with ethyl acetate and filtered to obtain compound 3 as a white solid (2.12 g).

Compound 4. Methyl 2-(2-((4-bromophenyl)amino)-2-oxoethoxy)benzoate (1 g, 2.75 mmol) is dissolved in 30 mL of a mixture of tetrahydrofuran and methanol (2:1). Potassium hydroxide (0.385 g, 6.87 mmol) is dissolved in 5 mL of water and then added to the reaction mixture. This mixture is then allowed to stir for 16 hours. Water is added. The aqueous solution was then extracted with diethyl ether, and the organic phase is discarded. The aqueous phase is then placed in a round bottomed flask with a stir bar, cooled in an ice bath, and then the pH was adjusted to approximately 3. A precipitate resulted that was immediately filtered off and dried to give compound 4 as a white solid (0.88 g).

Compound 6. 2-(2-((4-bromophenyl)amino)-2-oxoethoxy)benzoic acid (300 mg, 0.857 mmol) is dissolved in anhydrous DMF. Followed by stirring under ice-cooling, EDCI (246 mg, 1.286 mmol) was added, HOBT (174 mg, 1.286 mmol) is added, (S)-(+)-Tetrahydrofurfurylamine (102 mg, 1.028 mmol) is added, DIEA (277 mg, 2.143 mmol) is added. Then the reaction mixture is allowed to stir at room temperature for 3 h. Ice water was added. The mixture is extracted with EA. The organic phases are combined and washed with brine, dried, and concentrated in vacuo to give a yellow solid; the residue is purified by column chromatography (PE:EA, 1:1) to obtain compound 6 as a white solid (190 mg).

$^1$H NMR (400 MHz, CDCl3) δ 10.32 (s, 1H), 7.73 (d, J=8.8 Hz, 2H), 7.55 (dd, J=7.6, 1.6 Hz, 1H), 7.51-7.36 (m, 3H), 7.16-6.95 (m, 2H), 6.63 (s, 1H), 4.76 (s, 2H), 4.09 (qd, J=7.3, 3.3 Hz, 1H), 3.92-3.78 (m, 2H), 3.74 (dd, J=15.2, 6.9 Hz, 1H), 3.43-3.26 (m, 1H), 2.06 (dt, J=12.4, 6.8 Hz, 1H), 1.99-1.85 (m, 2H), 1.72-1.61 (m, 1H).

HPLC: purity @214 nm: 99.3%, @254 nm: 99.3%

MS Calcd.: 433.3, MS Found: 435.2.

Compound 8. 2-(2-((4-bromophenyl)amino)-2-oxoethoxy)benzoic acid (300 mg, 0.857 mmol) is dissolved in anhydrous DMF. Followed by stirring under ice-cooling, EDCI (246 mg, 1.286 mmol) was added, HOBT (174 mg, 1.286 mmol) is added, (R)-(−)-Tetrahydrofurfurylamine (102 mg, 1.028 mmol) was added, DIEA (277 mg, 2.143 mmol) was added. Then the reaction mixture is allowed to stir at room temperature for 3 h. Ice water is added. The mixture is extracted with EA. The organic phases are combined and washed with brine, dried, and concentrated in vacuo to give a yellow solid; the residue is purified by column chromatography (PE:EA, 1:1) to obtain compound 6 as a white solid (200 mg).

$^1$H NMR (400 MHz, CDCl3) δ 10.32 (s, 1H), 7.73 (d, J=8.8 Hz, 2H), 7.55 (dd, J=7.6, 1.4 Hz, 1H), 7.45 (dd,

J=17.7, 8.6 Hz, 3H), 7.15-6.96 (m, 2H), 6.62 (s, 1H), 4.76 (s, 2H), 4.09 (qd, J=7.4, 3.3 Hz, 1H), 3.85 (qd, J=6.6, 3.3 Hz, 2H), 3.74 (dd, J=15.0, 7.0 Hz, 1H), 3.45-3.23 (m, 1H), 2.05 (tt, J=24.4, 12.3 Hz, 1H), 1.97-1.89 (m, 2H), 1.72-1.61 (m, 1H).

HPLC: purity @214 nm: 99.7%, @254 nm: 99.8%

MS Calcd.: 433.3, MS Found: 435.2

2. Cell Treatment

Fibroblast cells from wild type (WT) and GCase mutant mice, homozygous V394L/V394L (4L/4L) and 4L/4L/with saposin C-/- (4L;C*) [13] were cultured in 10% Bovine Calf Serum/Dulbecco's Modified Eagle's medium (DMEM). The compounds were dissolved in Dimethyl sulfoxide (DMSO) at 5 mM as a stock solution and stored at −20° C. For cell treatment, the stock was diluted with DMEM and added to cells. The cells were incubated with the compounds for 5 days and changed with fresh media with the compound every two days.

3. Measuring GCase Activity

Cell pellets were collected and washed with Phosphate-buffered saline twice. The cell pellets were homogenized in 1% Na-taurocholate/1% Triton X-100 (Tc/Tx). GCase activity was determined fluorometrically with 4MU-Glc as substrate in 0.25% Tc/Tx diluted in 0.1M citrate phosphate (CP) buffer (pH 5.6) as described [7]. Protein concentrations of cells and tissues were determined by BCA assay using BSA as standard.

4. Immunoblot of GCase Protein

Cell pellets were collected and washed with Phosphate-buffered saline twice. The pellets were suspended in M-per lysis buffer. Freeze and thaw twice to break down the cell membrane. Protein concentration was determined by the bicinchoninic acid assay. The proteins were resolved on 4-12% NuPAGE gel (Invitrogen) and were transferred to PVDF membrane using iBlot 2 gel transfer device (Life Technologies) following manufactural instruction. The blotted membranes were incubated with Goat anti-mouse GCase (1:1000) in 1.5% BSA/1.5% milk/PBS buffer overnight at 4° C. followed by IRdye Donkey anti-Goat 1:5000. The signals were detected using LI-COR detection system according to manufacturer's instruction.

5. Immunofluorescence Staining

The cells grown on the chamber slides were fixed in 4% paraformaldehyde for 30 mins, followed by washing twice in Phosphate-buffered saline. The cells were permeablized with 0.3% Triton X-100 in Phosphate-buffered saline and washed with Phosphate-buffered saline for three times. After blocking for 30 min in 1.5% BSA/0.5% gelatin diluted in Phosphate-buffered saline, primary antibody, mouse anti-Lamp1 (1:200) and goat anti-mGCase (1:200) were applied to the cells and incubated overnight at 4° C. The signals were detected using Donkey anti-goat-FITC (1:500) and goat anti-mouse-Texas Red (1:500) to the cognate primary antibody. The stained cells were mounted with antifade containing DAPI.

6. Blood-Brain-Barrier Penetration Potential (Performed at Absorption Systems LLC)

MDR1-MDCK cell monolayers were grown to confluence on collagen-coated, microporous membranes in 12-well assay plates. The permeability assay buffer was Hanks' balanced salt solution containing 10 mM HEPES and 15 mM glucose at a pH of 7.4. The buffer in the receiver chamber also contained 1% bovine serum albumin. The dosing solution concentration was 5 µM of test article in the assay buffer. Cell monolayers were dosed on the apical side (A-to-B) or basolateral side (B-toA) and incubated at 37° C. with 5% CO2 in a humidified incubator. Samples were taken from the donor and receiver chambers at 120 minutes. Each determination was performed in duplicate. The flux of lucifer yellow was also measured post-experimentally for each monolayer to ensure no damage was inflicted to the cell monolayers during the flux period. All samples were assayed by LC-MS/MS using electrospray ionization.

The apparent permeability ($P_{app}$) and percent recovery were calculated as follows:

$$P_{app}=(dC_r/d_t)\times V_r/(A\times CA)$$

$$\text{Percent Recovery}=100\times((V_r\times C_r^{final})+(V_d\times C_d^{final}))/(V_d\times C_N)$$

Where, $dC_r/d_t$ is the slope of the cumulative concentration in the receiver compartment versus time in $\mu M \ s^{-1}$; $V_r$ is the volume of the receiver compartment in $cm^3$; $V_d$ is the volume of the donor compartment in $cm^3$; A is the area of the insert (1.13 $cm^2$ for 12-well); CA is the average of the nominal dosing concentration and the measured 120 minute donor concentration in µM; CN is the nominal concentration of the dosing solution in µM; Cr final is the cumulative receiver concentration in M at the end of the incubation period; Cd final is the concentration of the donor in M at the end of the incubation period.

Efflux ratio (ER) is defined as $P_{app}$ (B-to-A)/$P_{app}$ (A-to-B).

Results and Discussion

1. Compound Structure Design and Synthesis

Small molecule compounds were designed with the following structures. Compounds #6 and #8 were synthesized at Medicilon Inc.

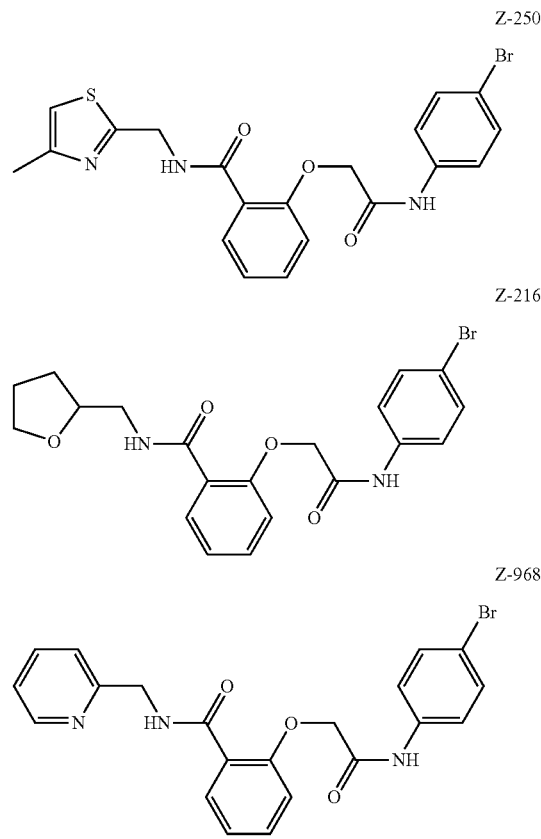

-continued

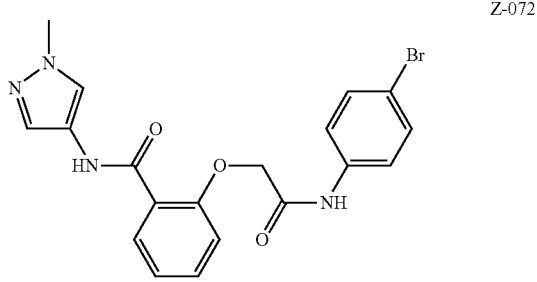

Z-072

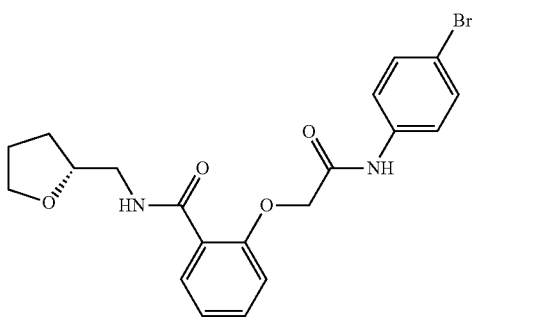

Compound 8

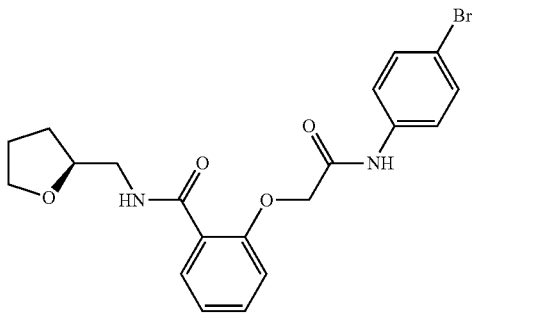

Compound 6

2. The Compounds have Chaperone Activity

Figure 2:
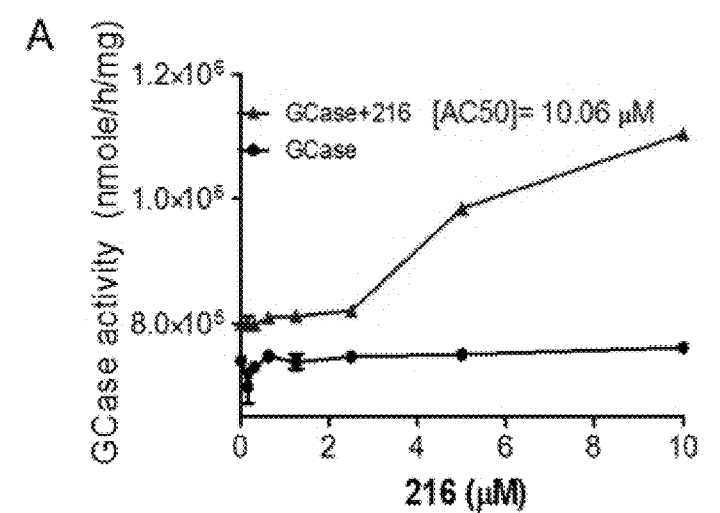
FIG. 2. Compound 216 is a non-inhibitory chaperone. Recombinant GCase was incubated with or without compound 216 at various concentration and GCase activity was determined. (A) 216 has activation effect on GCase with AC50=10.1 μM. Isofagomine is an inhibitor for GCase with IC 50=31.3 nM.
Figure 2:
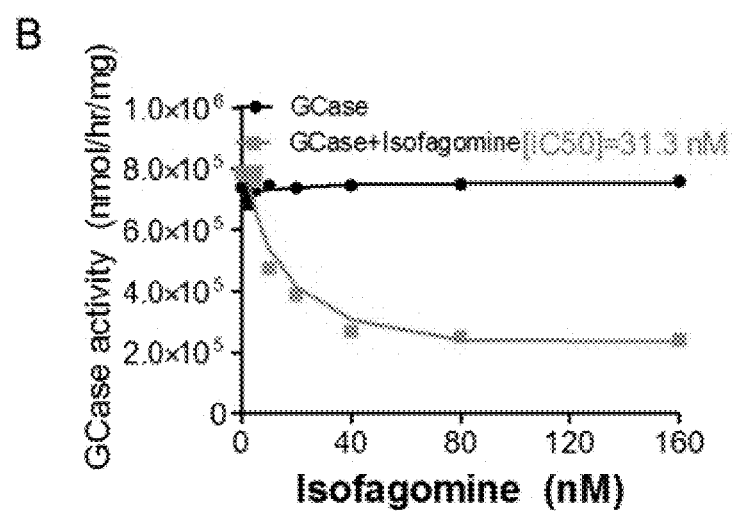

The chaperoning activity of the compounds was determined using WT and GCase mutant fibroblasts by measuring GCase activity and GCase protein levels and lysosomal localization [13]. Applicant screened small molecules compared to the control compound NCGC607 using mutant GCase (V394L) fibroblasts. Compound 216 has superior activation function on GCase and reduced toxicity compared to 607 (FIG. 1). Compared to the inhibitory chaperone isofagomine (IC50=31 nM), compound 216 (AC50=10 M) did not inhibit GCase (FIG. 2).

Figure 3:
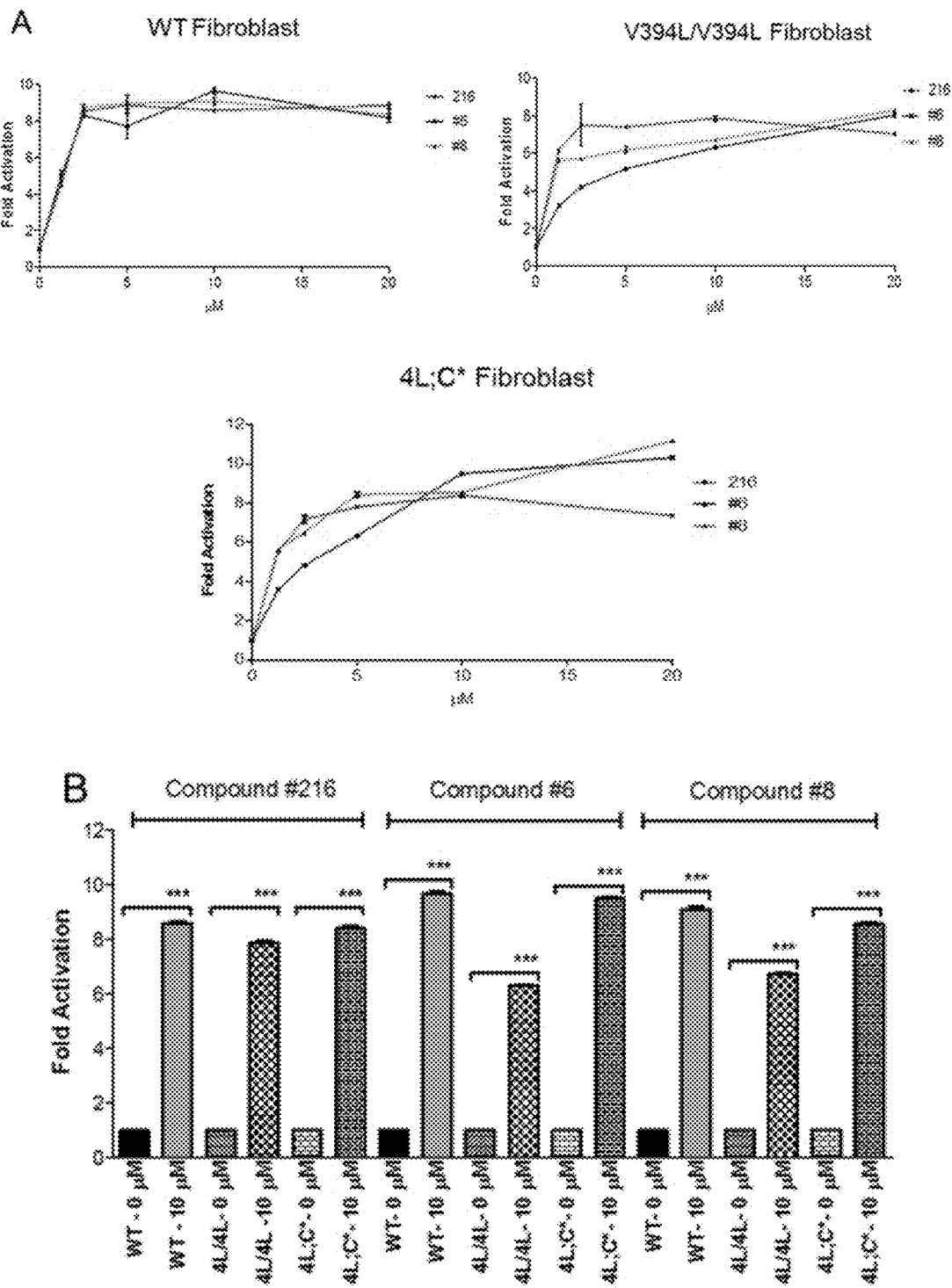
FIG. 3. Increased GCase activity in mouse fibroblasts treated with chaperone compounds (216, #6, and #8). (A) Fold activation of dose dependent increases of GCase activity in mouse WT, 4L/4L, and 4L;C* fibroblasts treated with 216, #6, or #8 for 5 days. (B) Significant increases of GCase activity (Fold change) in mouse WT, 4L/4L, and 4L;C* fibroblasts treated with 10 μM of each compound compared to corresponding untreated cells.
Figure 4:
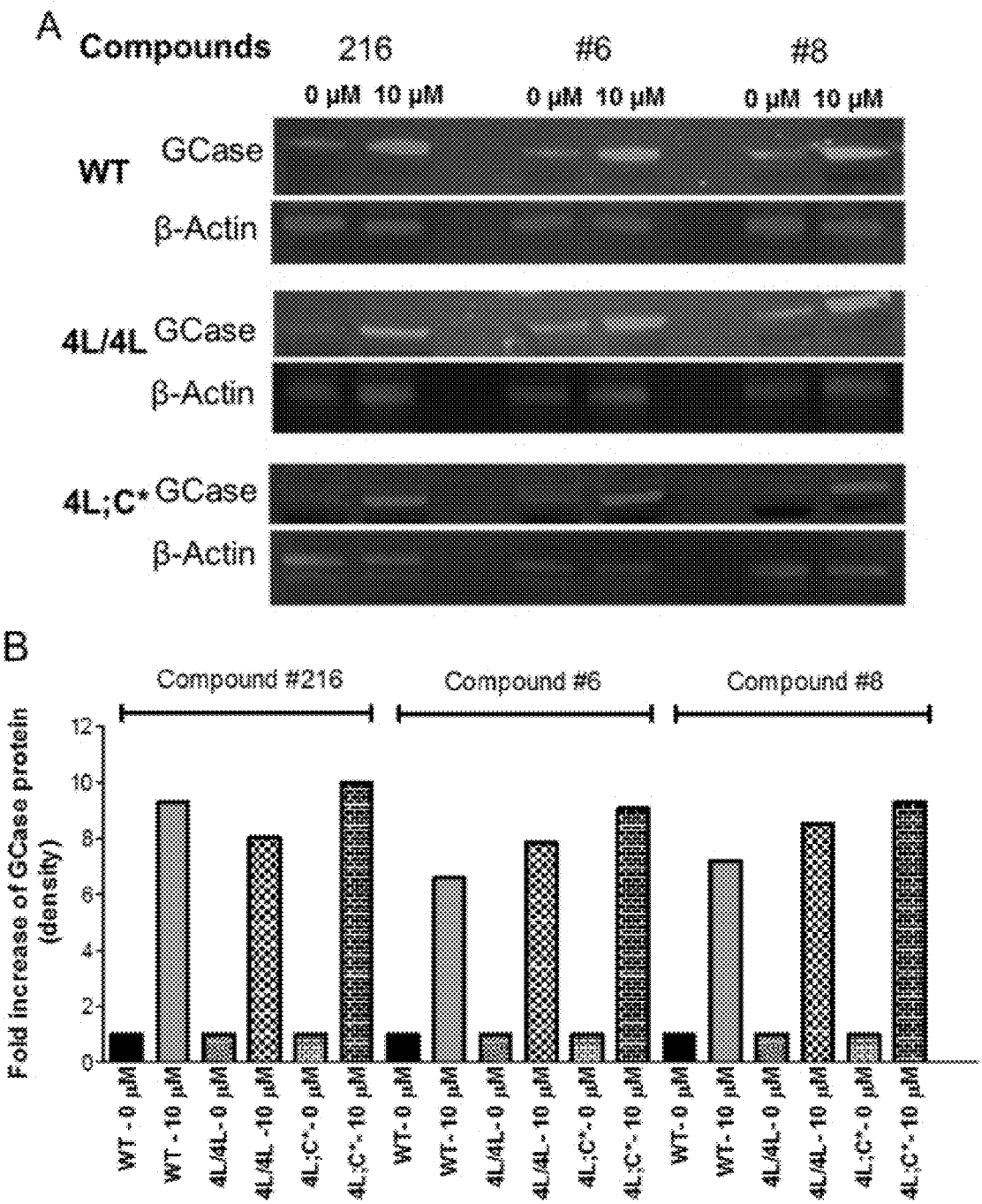
FIG. 4. Increased GCase protein in mouse fibroblasts treated with 10 μM chaperone compounds. (A) Immunoblot of GCase in WT, 4L/4L, and 4L;C* fibroblasts treated with 10 μM 216, #6, or #8, respectively, for 5 days. β-Actin is the loading control. (B) Quantitation of GCase protein density in immunoblots (A). GCase protein levels (Fold increase) were increased in 216, #6, or #8 treated WT, 4L/4L, and 4L;C* fibroblasts, respectively, compared to corresponding untreated cells.
Figure 5:
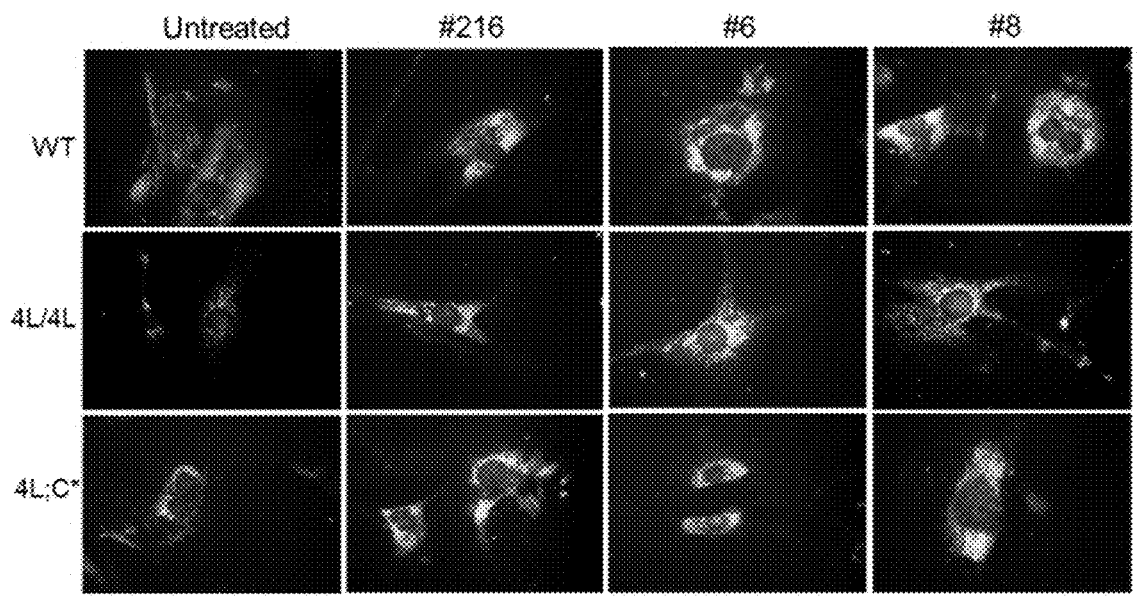
FIG. 5. Increased GCase protein in lysosomes of mouse fibroblasts treated with M chaperone compounds. (A) GCase (green) was co-stained with lysosomal marker, Lamp1 (red). Co-localization of GCase and Lamp1 (orange) indicates lysosomal localization of GCase. (B) Pearson index value shows enhanced lysosomal localization of GCase protein in 216, #6, or #8 treated WT, 4L/4L and 4L;C* fibroblasts, respectively, compared to corresponding untreated cells.
Figure 5:
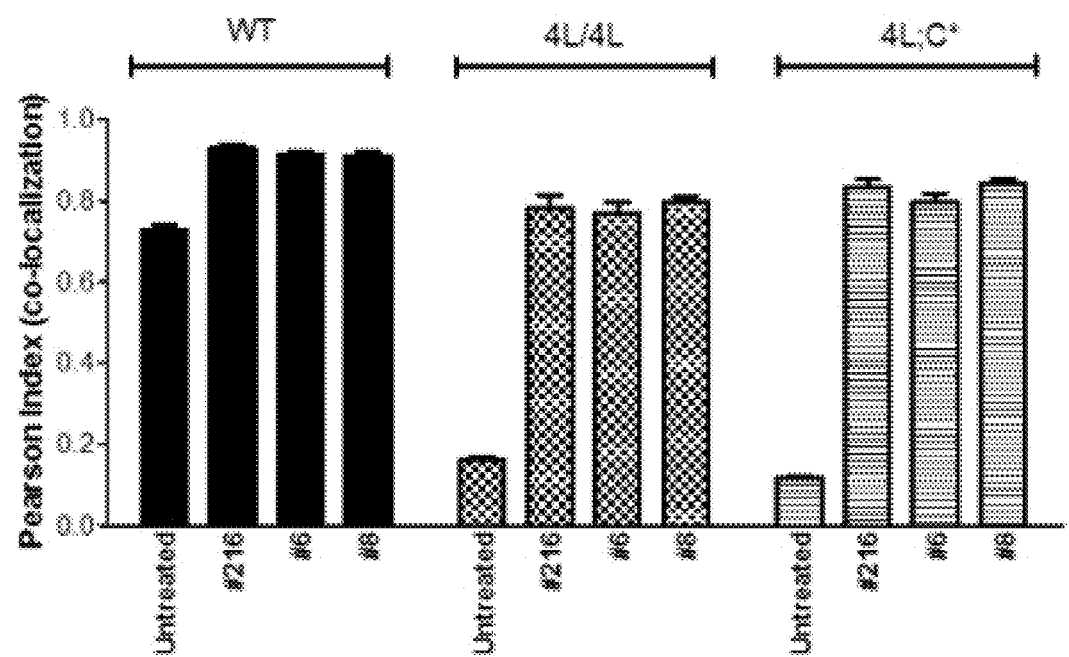
Figure 6:
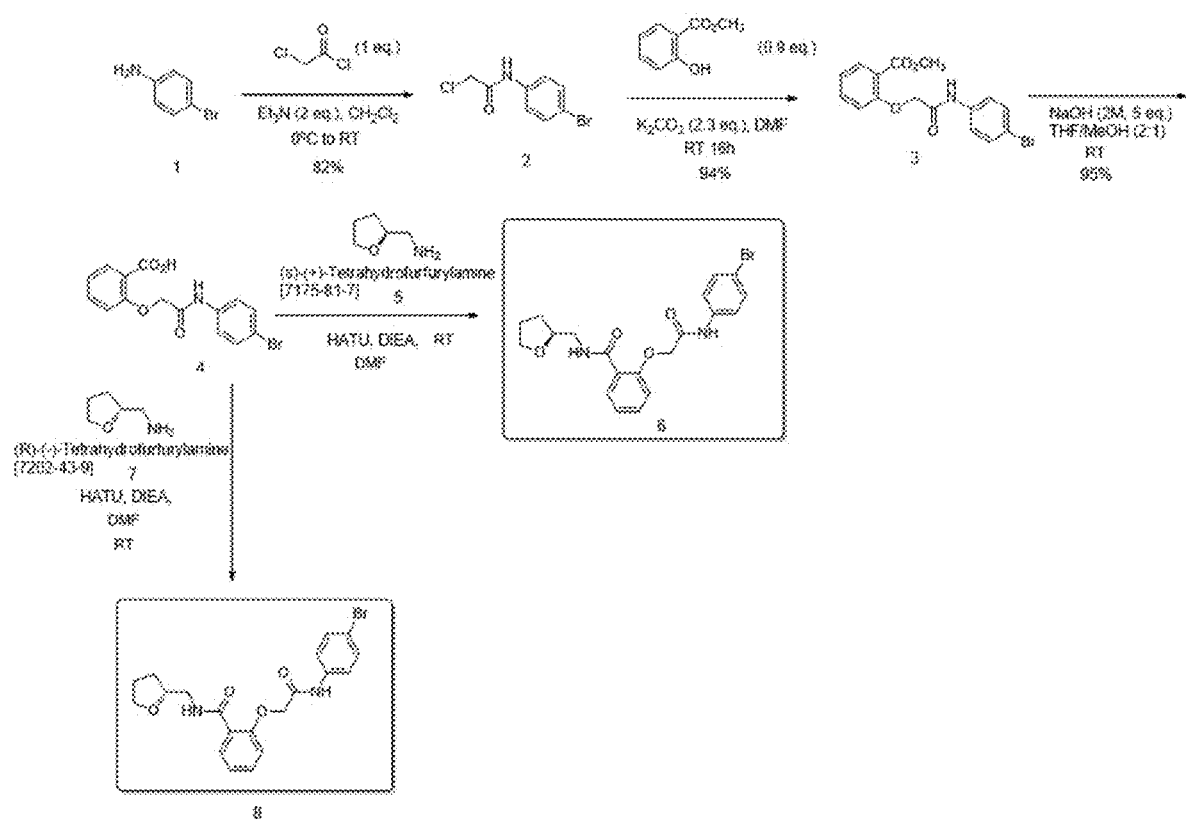
FIG. 6. Synthesis schemes for stereoisomer Compound 6 and Compound 8.
Figure 7:
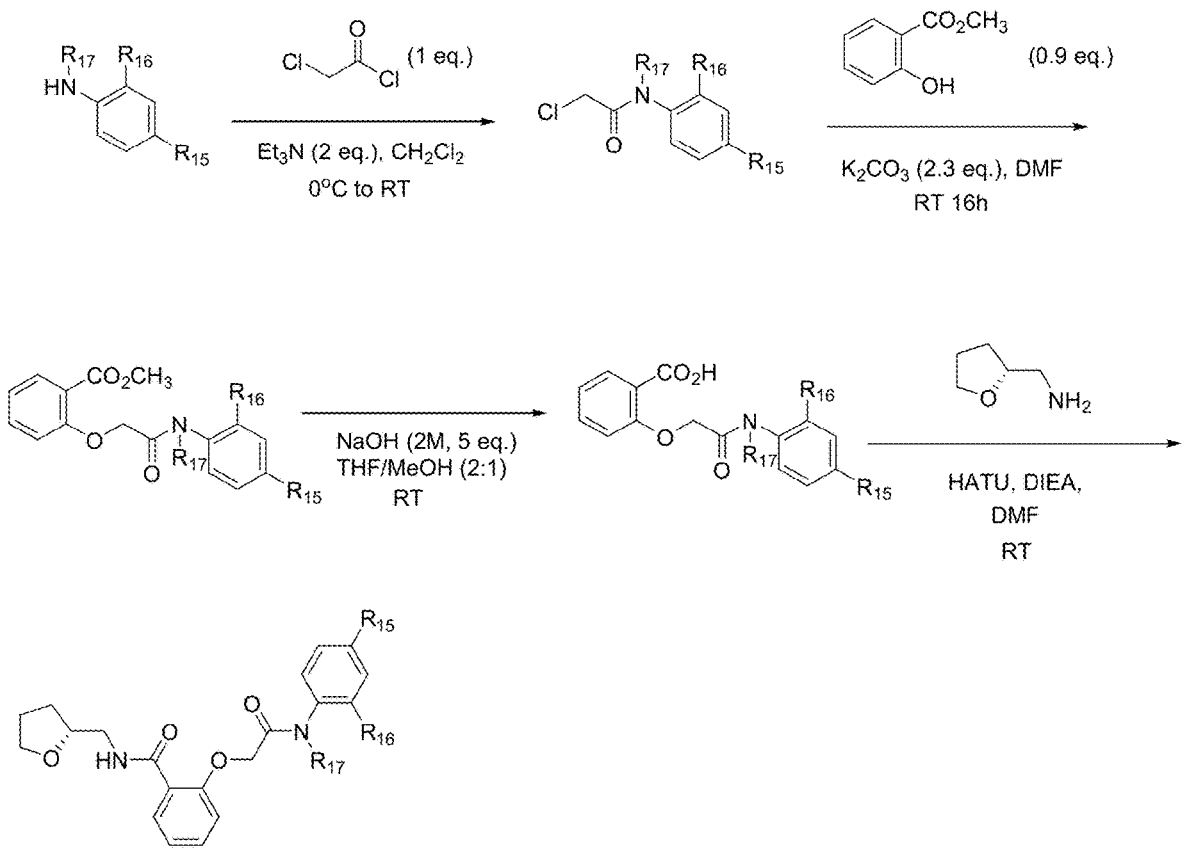
FIG. 7. General synthetic scheme for compound 1, 2, 3, 4, 5, 9 and 13.
Figure 8:
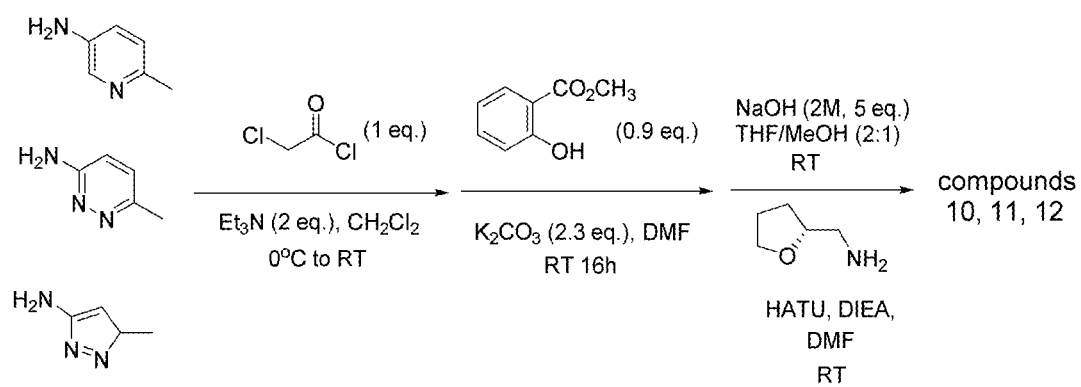
FIG. 8. General synthetic scheme for compound 10, 11 and 12.

Compound #6 and #8 are stereoisomers of 216. Applicant evaluated the effect of those three compounds on GCase activity (FIG. 3), protein level (FIG. 4) and lysosomal location (FIG. 5). All three compounds enhanced activity of WT and mutant GCase by 6-10 fold (FIG. 3). In WT fibroblast, 2.5 µM compound led to maximal activation, whereas 10 µM for both mutant cells achieving maximal activation (FIG. 3A). WT and mutant V394L GCase protein levels were increased with compounds treatment by 7-10 fold compared to untreated cells (FIG. 4). GCase in lysosome was determined by co-localization with Lamp1, a lysosomal marker (FIG. 5A). Enhanced lysosomal GCase signals were evident in WT and mutant cells treated with compounds. Pearson Index, a measure of co-localization of GCase and Lamp1 signals, indicate increased co-localization of two signals or lysosomal localization of GCase were in WT and mutant fibroblasts treated with compounds (FIG. 5B). These results demonstrated that compound 216 and its stereoisomers #6 and #8, have chaperoning properties for GCase.

3. CNS Drug Properties of Compound #8

Blood-brain barrier permeability ($P_{app}$) and efflux ratio of lead compound #8 was measured in vitro using the MDR1-MDCK assay. Compound #8 showed high brain penetration through the blood-brain-barrier with a $P_{app}$ of 32. 1×10$^{-6}$ cm/s and P-gp efflux ratio of 1.1, demonstrating CNS penetration property (Table 1).

TABLE 1

$P_{app}$ of compound #8 determined by MDR1-MDCK assay

| Test Article | Direction | Recovery (%) | $P_{app}$ (10$^{-6}$ cm/s) R1 | R2 | AVE | Efflux Ratio | Brain Penetration Classification |
|---|---|---|---|---|---|---|---|
| Compound 8 | A to B | 77 | 33.4 | 30.8 | 32.1 | 1.1 | High |
|  | B to A | 86 | 31.8 | 37 | 34.4 |  |  |

REFERENCES

1. Aymami J, Barril X, Rodriguez-Pascau L, Martinell M. Pharmacological chaperones for enzyme enhancement therapy in genetic diseases. Pharm Pat Anal. 2013; 2(1): 109-24.
2. Sun Y, Ran H, Liou B, Quinn B, Zamzow M, Zhang W, et al. Isofagomine in vivo effects in a neuronopathic Gaucher disease mouse. PloS one. 2011; 6(4):e19037. Epub 2011/05/03. doi: 10.1371/journal.pone.0019037. PubMed PMID: 21533102; PubMed Central PMCID: PMC3080394.
3. Richter F, Fleming S M, Watson M, Lemesre V, Pellegrino L, Ranes B, et al. A GCase chaperone improves motor function in a mouse model of synucleinopathy. Neurotherapeutics. 2014; 11(4):840-56. doi: 10.1007/s13311-014-0294-x. PubMed PMID: 25037721; PubMed Central PMCID: PMCPMC4391384.
4. DePaolo J, Goker-Alpan O, Samaddar T, Lopez G, Sidransky E. The association between mutations in the lysosomal protein glucocerebrosidase and parkinsonism. Movement disorders: official journal of the Movement Disorder Society. 2009; 24(11): 1571-8. Epub 2009/05/09. doi: 10.1002/mds.22538. PubMed PMID: 19425057; PubMed Central PMCID: PMC2736332.
5. Sidransky E, Nalls M A, Aasly J O, Aharon-Peretz J, Annesi G, Barbosa E R, et al. Multicenter analysis of glucocerebrosidase mutations in Parkinson's disease. The New England journal of medicine. 2009; 361(17): 1651-61. Epub 2009/10/23. doi: 10.1056/NEJMoa0901281. PubMed PMID: 19846850; PubMed Central PMCID: PMC2856322.
6. Mazzulli J R, Xu Y H, Sun Y, Knight A L, McLean P J, Caldwell G A, et al. Gaucher disease glucocerebrosidase and alpha-synuclein form a bidirectional pathogenic loop in synucleinopathies. Cell. 2011; 146(1):37-52. Epub 2011/06/28. doi: 10.1016/j.cell.2011.06.001. PubMed PMID: 21700325; PubMed Central PMCID: PMC3132082.
7. Sun Y, Liou B, Xu Y H, Quinn B, Zhang W, Hamler R, et al. Ex vivo and in vivo effects of isofagomine on acid beta-glucosidase variants and substrate levels in Gaucher disease. J Biol Chem. 2012; 287(6):4275-87. doi: 10.1074/jbc.M111.280016. PubMed PMID: 22167193; PubMed Central PMCID: PMCPMC3281716.
8. Khanna R, Benjamin E R, Pellegrino L, Schilling A, Rigat B A, Soska R, et al. The pharmacological chaperone isofagomine increases the activity of the Gaucher disease L444P mutant form of beta-glucosidase. FEBS J. 2010; 277(7):1618-38. doi: 10.1111/j.1742-4658.2010.07588.x. PubMed PMID: 20148966; PubMed Central PMCID: PMCPMC2874831.
9. Bendikov-Bar I, Maor G, Filocamo M, Horowitz M. Ambroxol as a pharmacological chaperone for mutant glucocerebrosidase. Blood Cells Mol Dis. 2013; 50(2): 141-5. doi: 10.1016/j.bcmd.2012.10.007. PubMed PMID: 23158495; PubMed Central PMCID: PMCPMC3547170.
10. Aflaki E, Borger D K, Moaven N, Stubblefield B K, Rogers S A, Patnaik S, et al. A New Glucocerebrosidase Chaperone Reduces alpha-Synuclein and Glycolipid Levels in iPSC-Derived Dopaminergic Neurons from Patients with Gaucher Disease and Parkinsonism. J Neurosci. 2016; 36(28):7441-52. doi: 10.1523/JNEUROSCI.0636-16.2016. PubMed PMID: 27413154; PubMed Central PMCID: PMCPMC4945664.
11. Marugan J J, Huang W, Motabar O, Zheng W, Xiao J, Patnaik S, et al. Non-iminosugar glucocerebrosidase small molecule chaperones. Medchemcomm. 2012; 3(1): 56-60. doi: 10.1039/C1MD00200G. PubMed PMID: 22606365; PubMed Central PMCID: PMCPMC3351140.
12. Patnaik S, Zheng W, Choi J H, Motabar O, Southall N, Westbroek W, et al. Discovery, structure-activity relationship, and biological evaluation of noninhibitory small molecule chaperones of glucocerebrosidase. J Med Chem. 2012; 55(12):5734-48. doi: 10.1021/jm300063b. PubMed PMID: 22646221; PubMed Central PMCID: PMCPMC3400126.
13. Sun Y, Liou B, Ran H, Skelton M R, Williams M T, Vorhees C V, et al. Neuronopathic Gaucher disease in the mouse: viable combined selective saposin C deficiency and mutant glucocerebrosidase (V394L) mice with glucosylsphingosine and glucosylceramide accumulation and progressive neurological deficits. Human molecular genetics. 2010; 19(6): 1088-97. Epub 2010/01/06. doi: 10.1093/hmg/ddp580. PubMed PMID: 20047948; PubMed Central PMCID: PMC2830832.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method of treating Parkinson's disease or Gaucher's disease in an individual in need thereof, comprising administering a compound selected from the group consisting of

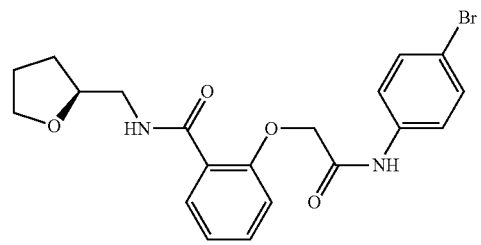 [SMILES: O=C(COc1ccccc1C(=O)NC[C@@H]1CCCO1)Nc1ccc(Br)cc1]

("Compound 6", 2-((4-bromophenylcarbamoyl) methoxy)-N—(((S)tetrahydrofuran-2-yl)methyl)benzamide));

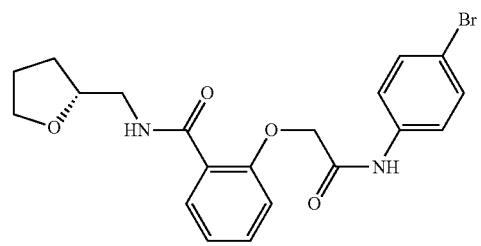 [SMILES: O=C(COc1ccccc1C(=O)NC[C@H]1CCCO1)Nc1ccc(Br)cc1]

("Compound 8", 2-((4-bromophenylcarbamoyl) methoxy)-N—(((R)-tetrahydrofuran-2-yl)methyl)benzamide));

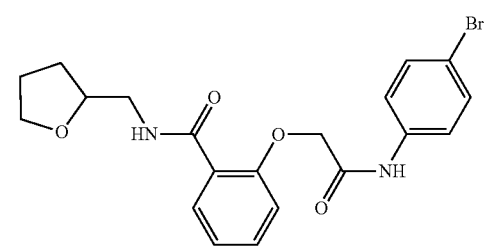 [SMILES: O=C(COc1ccccc1C(=O)NCC1CCCO1)Nc1ccc(Br)cc1]

("Compound Z-216"); and combinations thereof.

2. The method of claim 1, wherein said administration is oral administration.

3. The method of claim 1, wherein said compound is administered in an amount sufficient to functionally recover a mutant form of β-glucosidase enzyme ("GCase") in said individual by one or more of improving protein folding, stability, and trafficking to a lysosome.

4. The method of claim 1, further comprising administering a glucosylceramide synthase inhibitor.

5. The method of claim 4, wherein said glucosylceramide synthase inhibitor is selected from the group consisting of miglustat, eliglustat, venglustat, and combinations thereof.

6. The method of claim 1, further comprising administering β-glucosidase enzyme to said individual.

7. The method of claim 6, further comprising administering a glucosylceramide synthase inhibitor.

8. The method of claim 7, wherein said glucosylceramide synthase inhibitor is selected from the group consisting of miglustat, eliglustat, venglustat, and combinations thereof.

* * * * *